(12) United States Patent
Miyamoto

(10) Patent No.: US 10,175,911 B2
(45) Date of Patent: Jan. 8, 2019

(54) IMAGE FILE DISTRIBUTION APPARATUS, IMAGE FILE RECOVERY APPARATUS, IMAGE FILE DISTRIBUTION METHOD, IMAGE FILE RECOVERY METHOD, IMAGE FILE DISTRIBUTION PROGRAM, IMAGE FILE RECOVERY PROGRAM, AND RECORDING MEDIUM STORING PROGRAM

(71) Applicant: FUJIFILM Corporation, Tokyo (JP)

(72) Inventor: Kentaro Miyamoto, Tokyo (JP)

(73) Assignee: FUJIFILM Corporation, Minato-ku, Tokyo (JP)

( * ) Notice: Subject to any disclaimer, the term of this patent is extended or adjusted under 35 U.S.C. 154(b) by 0 days.

(21) Appl. No.: 15/709,534

(22) Filed: Sep. 20, 2017

(65) Prior Publication Data

US 2018/0004424 A1   Jan. 4, 2018

Related U.S. Application Data

(63) Continuation of application No. PCT/JP2016/057909, filed on Mar. 14, 2016.

(30) Foreign Application Priority Data

Mar. 23, 2015   (JP) ................................ 2015-058907

(51) Int. Cl.
   *G06F 12/00*   (2006.01)
   *G06F 3/06*    (2006.01)
   (Continued)

(52) U.S. Cl.
   CPC .............. *G06F 3/065* (2013.01); *G06F 3/067* (2013.01); *G06F 3/0619* (2013.01);
   (Continued)

(58) Field of Classification Search
   CPC ...... G06F 3/065; G06F 3/0619; G06F 3/0643; G06F 3/067; G06F 12/00; G06F 19/00; G06F 21/6218; G09C 1/00; H04L 9/085
   See application file for complete search history.

(56) References Cited

U.S. PATENT DOCUMENTS

2007/0239615 A1* 10/2007 Matsuzaki ....... G06K 19/07749
                                                                705/55
2014/0079322 A1   3/2014 Yamaji

FOREIGN PATENT DOCUMENTS

JP   2003-132234 A   5/2003
JP   2007-102672 A   4/2007
(Continued)

OTHER PUBLICATIONS

Kurihara J et al: "A Fast (k,L,n)-Threshold Ramp Secret Sharing Scheme", IEICE Trans, Fundamentals, vol. E92-A, No. 8, Published: Aug. 2009; pp. 1808-1821 (14 pages total).
(Continued)

*Primary Examiner* — Shawn X Gu
(74) *Attorney, Agent, or Firm* — Sughrue Mion, PLLC

(57) ABSTRACT

Provided are an image file distribution apparatus, an image file recovery apparatus, an image file distribution method, an image file recovery method, an image file distribution program, an image file recovery program, and a recording medium storing the program which can prevent a relatively large increase in the amount of data of an image file even when an (k, n) secret sharing scheme with high security is used. For example, distributed tag information is obtained from tag information of the image file by a (k, n)-threshold secret sharing scheme. For example, distributed image data is obtained from image data by a (k, L, n)-threshold ramp secret sharing scheme. For example, the distributed tag information and the distributed image data are combined to obtain combined data. Since the amount of data in the tag
(Continued)

information is small, the use of the (k, n) secret sharing scheme does not cause a large increase in the amount of data. Since the (k, L, n)-threshold ramp secret sharing scheme does not cause a large increase in the amount of data, an increase in the total amount of data in the image data is relatively small.

6 Claims, 12 Drawing Sheets

(51) Int. Cl.
    *G09C 1/00*     (2006.01)
    *G06F 19/00*     (2018.01)
    *G06F 21/62*     (2013.01)
    *H04L 9/08*     (2006.01)

(52) U.S. Cl.
    CPC ............ *G06F 3/0643* (2013.01); *G06F 12/00* (2013.01); *G06F 19/00* (2013.01); *G06F 21/6218* (2013.01); *G09C 1/00* (2013.01); *H04L 9/085* (2013.01)

(56) References Cited

FOREIGN PATENT DOCUMENTS

| | | |
|---|---|---|
| JP | 2007-189345 A | 7/2007 |
| JP | 2011-248711 A | 12/2011 |
| JP | 2012-010052 A | 1/2012 |
| JP | 2013-20313 A | 1/2013 |
| JP | 2014-075778 A | 4/2014 |
| WO | 2014078755 A1 | 5/2014 |

OTHER PUBLICATIONS

Jay J. Wylie et al; "Selecting the right data distribution scheme for a survivable storage system", Carnegie Mellon University, Research Showcase @ CMU, Computer Science Department, School of Computer Science, 24 pages total, May 2001.

Communication dated Dec. 14, 2017, issued by the European Patent Office in counterpart application No. 16768504.9.

International Preliminary Report on Patentability, dated Sep. 26, 2017 from the International Bureau in counterpart International application No. PCT/JP2016/057909.

Yasushi Matsumura, "Designing of External Medical Record Documents Reposition System using Secret Share Scheme" Japan Journal of Medical Information, vol. 33, Nov. 23, 2013, 4 pages.

Kohei Horiuchi, "MyCloud: A Secret Sharing Storage System Combining Several Vendors' Data Cloud Services", Information Processing Society of Japan Symposium, Programming Symposium, Jan. 12, 2010, 4 pages.

Adi Shamir, "How to share a Secret", Programming Techniques, Communications of the ACM, vol. 22, No. 11, Nov. 1979, pp. 612-613.

Hirosuke Yamamoto, "On Secret Sharing Systems Using (k L n) Threshold Scheme", Transactions of the Institute of Electronics and Communication Engineers of Japan, vol. 168-A, No. 9, pp. 945-952, 1985.

International Search Report for PCT/JP2016/057909 dated May 24, 2016 [PCT/ISA/210].

Written Opinion for PCT/JP2016/057909 dated May 24, 2016 [PCT/ISA/237] P.

\* cited by examiner

FIG. 4

| DICOM FILE No. | DICOM FILE NAME | RECORDING DESTINATION 1 | ... | RECORDING DESTINATION 3 |
|---|---|---|---|---|
| 1 | /home/image/patient01.dcm | ¥¥192.168.0.1¥data¥ao3addm | ... | ¥¥192.168.0.4¥data¥tadxrfg |
| 2 | /home/image2/patient02.dcm | ¥¥192.168.0.1¥data¥diagrwaa | ... | ¥¥192.168.0.4¥data¥gacrdaa |
| | | | ... | ... |

IMAGE FILE DISTRIBUTION APPARATUS, IMAGE FILE RECOVERY APPARATUS, IMAGE FILE DISTRIBUTION METHOD, IMAGE FILE RECOVERY METHOD, IMAGE FILE DISTRIBUTION PROGRAM, IMAGE FILE RECOVERY PROGRAM, AND RECORDING MEDIUM STORING PROGRAM

CROSS-REFERENCE TO RELATED APPLICATIONS

This application is a Continuation of PCT International Application No. PCT/JP2016/057909 filed on Mar. 14, 2016, which claims priority under 35 U.S.C. § 119(a) to Japanese Patent Application No. 2015-058907 filed Mar. 23, 2015. Each of the above application(s) is hereby expressly incorporated by reference, in its entirety, into the present application.

BACKGROUND OF THE INVENTION

1. Field of the Invention

The present invention relates to an image file distribution apparatus, an image file recovery apparatus, an image file distribution method, an image file recovery method, an image file distribution program, an image file recovery program, and a recording medium storing the program.

2. Description of the Related Art

When a very large amount of data is stored in storage device, the cost of the storage device increases. Therefore, the cost of storing data can be reduced by a cloud storage server that is provided on the Internet. However, it is pointed out that the cloud storage server has a security problem. In particular, when a cloud is used, the task is to secure data. For example, the following have been proposed in order to improve security: a technique that distributes a plurality of partial data items to a plurality of data centers and stores the partial data items in the data centers, using a secret sharing scheme (JP2013-020313A); and an apparatus that backs up data (JP2007-102672A 2).

There are various types of secret sharing schemes. A (k, n)-threshold secret sharing scheme (A. Shamir. "How to Share a Secret", Comm. Assoc. Comput. Mach., Vol. 22, no. 11, pp. 612-613 (Nov. 1979)) distributes secret information into n distributed data items, collects k (k is equal to or greater than 2 and equal to or less than n) distributed data items among the n distributed data items, and recovers the k distributed data items. A (k, n)-threshold secret sharing scheme is a perfect secret sharing scheme and has information-theoretic security. Therefore, even when k−1 distributed data items less than a threshold value are acquired, a clue about secret information does not leak. However, in the (k, n)-threshold secret sharing scheme, the size of the divided data is equal to the size of the original secret data. Therefore, the (k, n)-threshold secret sharing scheme has the problem that the total amount of divided. data is n times more than the amount of original secret data and the amount of data increases. In order to solve the problem of the (k, n)-threshold secret sharing scheme, a (k, L, n)-threshold ramp secret sharing scheme (Hirosuke Yamamoto, "(k, L, n)-Threshold Secret Sharing System", Transactions of the Institute of Electronics and Communication Engineers of Japan, vol. 168-A, No. 9, pp. 945-952, 1985) that can reduce the amount of divided data has been proposed. The (k, L, n)-threshold ramp secret sharing scheme (Hirosuke Yamamoto, "On Secret Sharing Systems Using (k L n) Threshold. Scheme", Transactions of the institute of Electronics and Communication Engineers of Japan, vol. 168-A, No. 9, pp. 945-952, 1985) compresses the size of distributed data to 1/L instead of reducing security (information-theoretic security up to k-L) a little. The (k, L, n)-threshold ramp secret sharing scheme is the same as the (k, n)-threshold secret sharing scheme in that it collects k or more divided data items among n divided data items and recovers the original secret data.

SUMMARY OF THE INVENTION

In contrast, in a case in which the number of collected divided data items is equal to or less than (k−L) (1≤L≤k), it is difficult to completely recover and estimate secret data from the divided data. However, in a case in which the number of collected divided data items is less than k and is greater than (k-L), the information of secret data is partially obtained. As a result, the (k, L, n)-threshold ramp secret sharing scheme has the problem that security is lower than that in the (k, n)-threshold secret sharing scheme.

An object of the invention is to prevent a relatively large increase in the amount of data even when a (k, n)-threshold secret sharing scheme with high security is used.

According to a first aspect of the invention, there is provided an image file distribution apparatus comprising: a (k, n)-threshold secret sharing device {(k, n)-threshold secret sharing means} for distributing tag information recorded in a tag information recording region of an image file into a plurality of first distributed tag information items, using a (k, n)-threshold secret sharing scheme; a (k, L, n)-threshold ramp secret sharing device {(k, L, n)-threshold ramp secret sharing means} for distributing image data recorded in an image data recording region of the image tile into a plurality of second distributed image data items, using a (k, L, n)-threshold ramp secret sharing scheme; a distributed tag information transmission device (distributed tag information transmission means) for transmitting each of the plurality of first distributed tag information items distributed by the (k, n)-threshold secret sharing device to different storage servers, and a distributed image data transmission device (distributed image data transmission means) for transmitting each of the plurality of second distributed image data items distributed by the (k, L, n)-threshold ramp secret sharing device to different storage servers.

The first aspect of the invention also provides an image file distribution method. That is, this method comprises: allowing a (k, n)-threshold secret sharing device to distribute tag information recorded in a tag information recording region of an image file into a plurality of first distributed tag information items, using a (k, n)-threshold secret sharing scheme; allowing a (k, L, n)-threshold ramp secret sharing device to distribute image data recorded in an image data recording region of the image file into a plurality of second distributed image data items, using a (k, L, n)-threshold ramp secret sharing scheme; allowing distributed tag information transmission to transmit each of the plurality of first distributed tag information items distributed by the (k, n)-threshold secret sharing device to different storage servers; and allowing a distributed image data transmission device to transmit each of the plurality of second distributed image data items distributed by the (k, L, n)-threshold ramp secret sharing device to different storage servers. In addition, the first aspect of the invention provides a computer readable program that controls a computer of an image file distribution apparatus and a (non-transitory) recording medium that stores the program.

The image file distribution apparatus may further comprise a combination device (combination means) for combining each of the distributed tag information items distributed by the (k, n)-threshold secret sharing device with each of the distributed image data items distributed by the (k, L, n)-threshold ramp secret sharing device to generate combined data. In this case, the distributed tag information transmission device and the distributed image data transmission device transmit the combined data generated by the combination device to different storage servers.

The number of first distributed tag information items distributed by the (k, n)-threshold secret sharing device may be different from the number of second distributed image data items distributed by the (k, L, n)-threshold ramp secret sharing device.

For example, the distributed image data transmission device transmits the plurality of second distributed image data items after the distributed tag information transmission device transmits the plurality of first distributed tag information items.

The image file distribution apparatus may further comprise: a determination device (determination device) for determining whether a rate of utilization of a communication line which is used to transmit the plurality of second distributed image data items by the distributed image data transmission device is less than a threshold value. In this case, as the determination device determines that the rate of utilization of the communication line is less than the threshold value, the distributed image data transmission device transmits the plurality of second distributed image data items.

The image file distribution apparatus may further comprise a distributed tag information storage device (distributed tag information storage means) for storing at least one of the plurality of first distributed tag information items distributed by the (k, n)-threshold secret sharing device. In this case, the distributed tag information transmission device transmits each of the distributed tag information items other than the distributed tag information item stored in the distributed tag information storage device among the plurality of first distributed tag information items to different storage servers.

For example, the image file is a DICOM tile.

The storage server to which the distributed tag information is transmitted by the distributed tag information transmission device may be different from the storage server to which the distributed image data is transmitted by the distributed image data transmission device.

According to a second aspect of the invention, there is provided an image file recovery apparatus comprising: a distributed tag information reading device for reading a plurality of first distributed tag information items which have been obtained by distributing tag information recorded in a tag information recording region of an image file, using a (k, n)-threshold secret sharing scheme, and have been stored in different storage servers; a distributed image data reading device for reading a plurality of second distributed image data items which have been obtained by distributing image data recorded in an image data recording region of the image file, using a (k, L, n)-threshold ramp secret sharing scheme, and have been stored in different storage servers; a distributed tag information recovery device (distributed tag information recovery means) for recovering the plurality of first distributed tag information items read by the distributed tag information reading device, using the (k, n)-threshold secret sharing scheme; and a distributed image data recovery device (distributed image data recovery means) for recovering the plurality of second distributed image data items read by the distributed image data reading device, using the (k, L, n)-threshold ramp secret sharing scheme.

The second aspect of the invention also provides an image file recovery method. That is, this method comprises: allowing a distributed tag information reading device to read a plurality of first distributed tag information items which have been obtained by distributing tag information recorded in a tag information recording region of an image file, using a (k, n)-threshold secret sharing scheme, and have been stored in different storage servers; allowing a distributed image data reading device to read a plurality of second distributed image data items which have been obtained by distributing image data recorded in an image data recording region of the image tile, using a (k, L, n)-threshold ramp secret sharing scheme, and have been stored in different storage servers; allowing a distributed tag information recovery device to recover the plurality of first distributed tag information items read by the distributed tag information reading device, using the (k, n)-threshold secret sharing scheme; and allowing a distributed image data recovery device to recover the plurality of second distributed image data items read by the distributed image data reading device, using the (k, L, n)-threshold ramp secret sharing scheme. In addition, the second aspect of the invention provides a program that can be read by a computer of an image file recovery apparatus and a (non-transitory) recording medium that stores the program.

The image file recovery apparatus may further comprise an image data reading stop device (image data reading stop means) for stopping the reading of the plurality of second distributed image data items by the distributed image data reading device.

The image file recovery apparatus may further comprise an image file generation device (image file generation means) for generating the image file from the distributed tag information recovered by the distributed tag information recovery device and the distributed image data recovered by the distributed image data recovery device.

In this case, the image file is, for example, a DICOM file.

According to the first aspect of the invention, the tag information of the image file is distributed into a plurality of first distributed tag information items by the (k, n)-threshold secret sharing scheme. The plurality of first distributed tag information items are transmitted to different storage servers and are stored in the storage servers. In addition, the image data of the image file is distributed into a plurality of second image data items by the (k, L, n)-threshold ramp secret sharing scheme. The plurality of second image data items are transmitted to different storage servers and are stored in the storage servers. The security of the (k, n)-threshold secret sharing scheme is higher than that of the (k, L, n) threshold ramp sharing scheme. The amount of data in the (k, n)-threshold secret sharing scheme is more than that in the (k. L, n)-threshold ramp secret sharing scheme. In contrast, the security of the (k, L, n)-threshold ramp secret sharing scheme is lower than that of the (k, n)-threshold secret sharing scheme. The amount of data after distribution in the (k, L, n)-threshold ramp secret sharing scheme is less than that in the (k, n)-threshold secret sharing scheme. According to the invention, the image data that originally has a large size is distributed by the (k, L, n)-threshold ramp secret sharing scheme in which the amount of data after distribution is small. Therefore, it is possible to suppress a relatively large increase in the amount of data. Since tag information is more important than image data, the tag information is distributed by the (k, n) sharing scheme with high security such that data does not leak. Since the original amount of data in the tag information is small, the tag information is distributed by the (k, n) sharing scheme. In this case, even when the amount of data is large, the rate of increase in the amount of data is less than that in a case in which image data is distributed by the (k, n) sharing scheme. Therefore, it is possible to guarantee the security of important tag information while suppressing an increase in the amount of data after distribution.

According to the second aspect of the invention, the distributed tag information and the distributed image data distributed by the first aspect of the invention are read. The read. distributed tag information and the read distributed image data are recovered. The tag information and the image data before distribution are obtained.

BRIEF DESCRIPTION OF THE DRAWINGS

FIG. 4 is a table storing the address of a recording destination of combined data.

DESCRIPTION OF THE PREFERRED EMBODIMENTS

Figure 1:
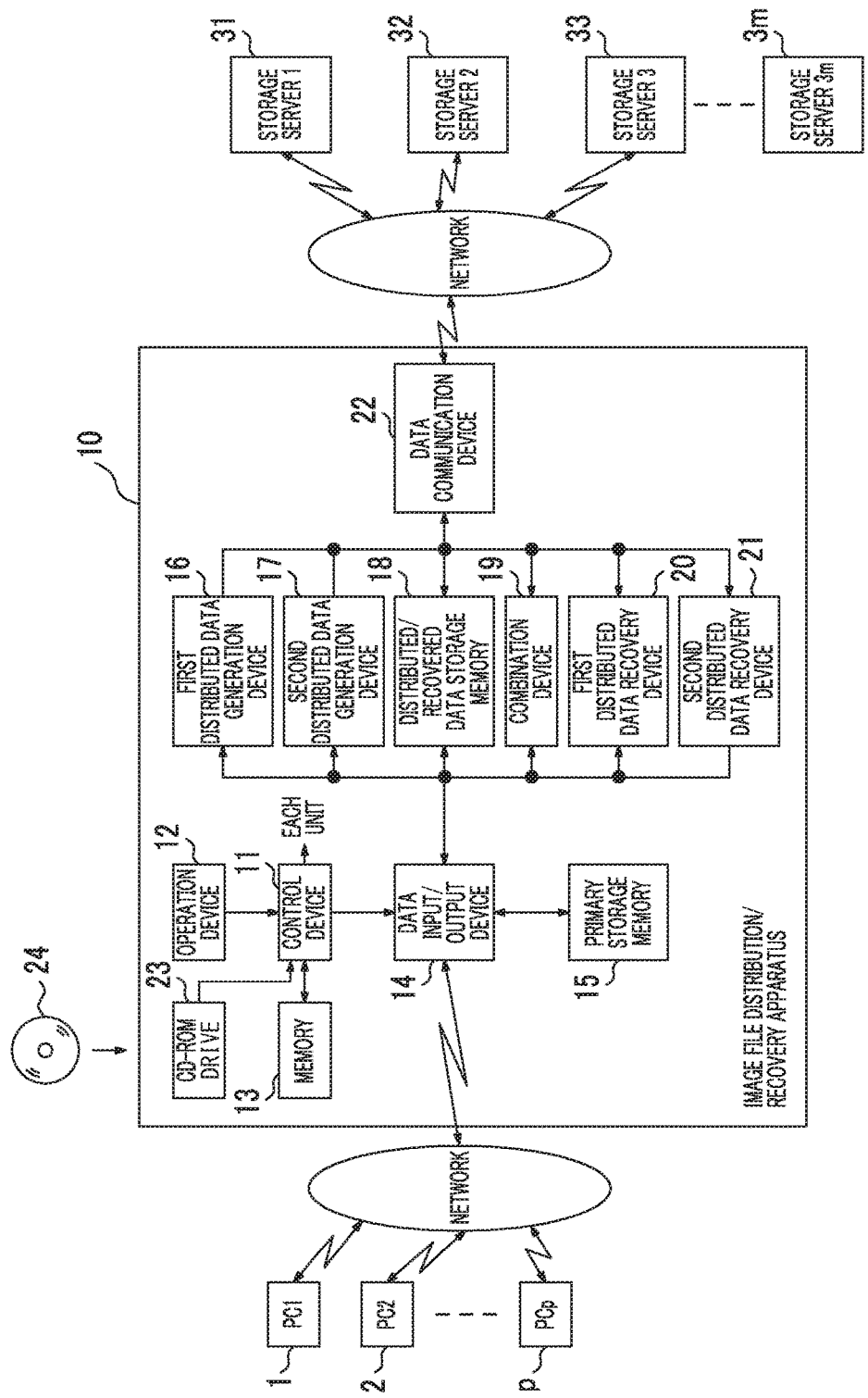
FIG. 1 is a block diagram illustrating the electric configuration of an image file distribution/recovery apparatus.
Figure 2:
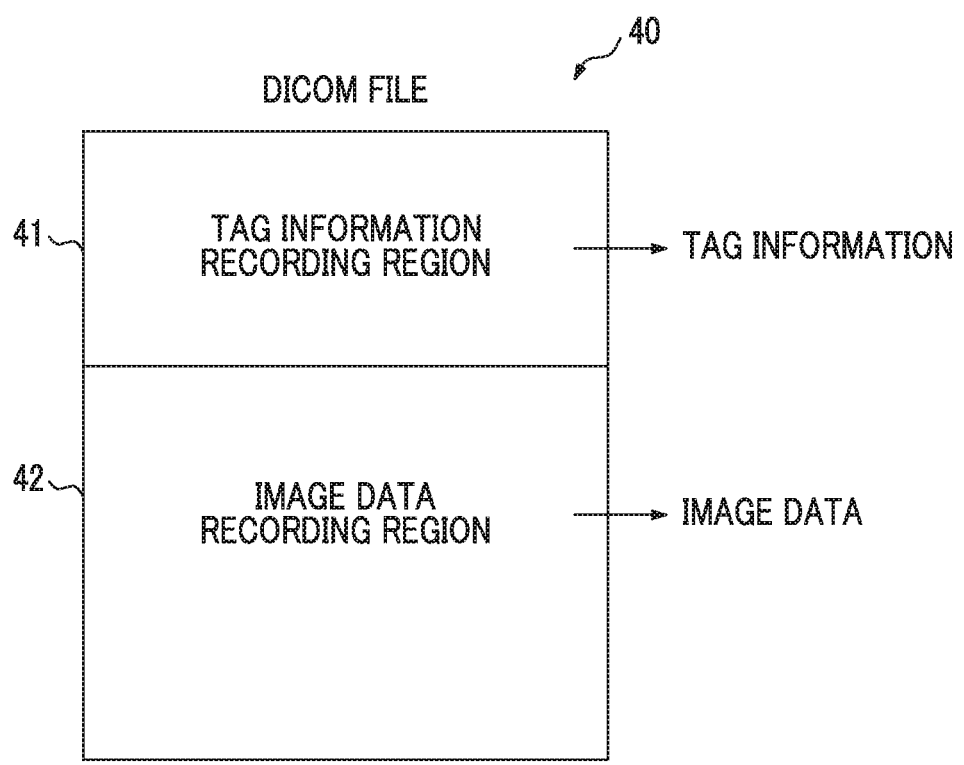
FIG. 2 illustrates the file structure of a DICOM file.
Figure 3:
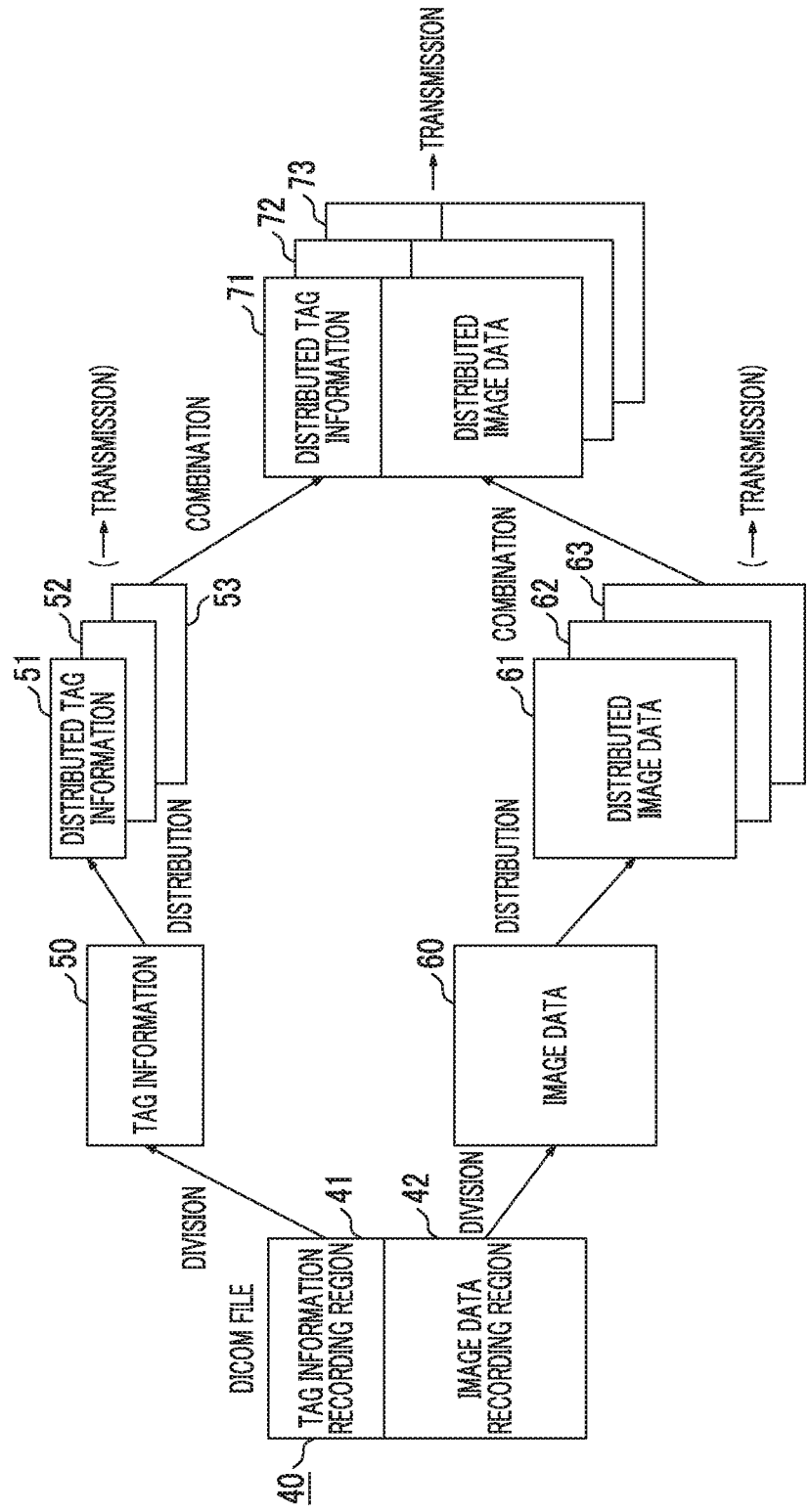
FIG. 3 illustrates an aspect in which an image file is distributed.

FIG. 1 illustrates an embodiment of the invention and is a block diagram mainly illustrating the electric configuration of an image file distribution/recovery apparatus 10. FIG. 2 illustrates the file structure of a digital imaging and communication in medicine (DICOM) file 40. FIG. 3 illustrates an aspect in Which the DICOM file 40 is distributed by the image file distribution/recovery apparatus.

The image file distribution/recovers apparatus 10 (an image file distribution apparatus and an image file recovery apparatus) distributes an image file using a secret sharing scheme. The image file distribution/recovery apparatus IC) according to this embodiment can perform distribution, using a (k, n)-threshold secret sharing scheme and a (k, L, n)-threshold ramp secret sharing scheme. The (k, n)-threshold secret sharing scheme distributes secret information into n distributed data items, collects k (k is equal to or greater than 2 and equal to or less than n) distributed data items among then distributed data items, and recovers the k distributed data items. The (k, n)-threshold secret sharing scheme is a perfect secret sharing scheme and has information-theoretic security. Therefore, even when k−1 distributed data items less than a threshold value are acquired, a clue about secret information does not leak. The (k, L, n)-threshold ramp secret sharing scheme compresses the size of distributed data to while reducing security (information-theoretic security up to k−L) a little. In these sharing schemes, n is a distribution number and k is a threshold value.

The (k, n)-threshold secret sharing scheme includes, for example, any type of scheme, such as a secret sharing scheme, a threshold sharing scheme, a secret division scheme, a. threshold value division scheme, or a threshold secret division scheme as long as it distributes secret information into n distributed data items, collects k (k is equal to or greater than 2 and equal to or less than n) distributed data items among the n distributed data items, and recovers the k distributed data items. Similarly, the (k, L, n)-threshold ramp secret sharing scheme includes any type of scheme as long as it compresses the size of distributed data to 1/L while reducing security (information-theoretic security up to k-L) a little.

The image file distribution/recovery apparatus 10 can communicate with p personal computers 1 to p through a network and can communicate with m storage servers 31 to 3m through the network.

The overall operation of the image file distribution/recovery apparatus 10 is controlled by a control device 11.

The image file distribution/recovery apparatus 10 includes a compact disc read only memory (CD-ROM) drive 23. When a compact disc read only memory (CD-ROM) 24 (recording medium) storing a program, which will be described below, is inserted into the image file distribution/ recovery apparatus 10, the program stored in the CD-ROM 24 is read and installed in the image file distribution/ recovery apparatus 10. The program is not limited to the recording medium, such as the CD-ROM 24, and may be stored in other recording media, such as a memory card, or may be downloaded and installed in the image file distribution/recovery apparatus 10 through the network.

The image file distribution/recovery apparatus 10 includes an operation device 12 that is operated by a user. Commands that are input to the operation device 12 are transmitted to the control device 11. In addition, a memory 13 that stores, for example, data is connected to the control device 11.

In this embodiment, the DICOM file 40 in which, for example, roentgen image data of a patient is stored as secret information is distributed. However, the invention is not limited to the DICOM file 40 and other files may be distributed.

Referring to FIG. 2, the DICOM file 40 includes a tag information recording region 41 and an image data recording region 42.

Medical image data, such as roentgen image data, is recorded in the image data recording region 42.

Tag information (management information) about a patient corresponding to an image indicated by the image data recorded in the image data, recording region 42, such as a patient name or a patient ID, is recorded in the tag information recording region 41.

Referring to FIG. 1 and FIG. 3, the DICOM file 40 is transmitted from any one of the personal computers 1 to n and is input to a data input/output device 14 of the image file distribution recovery apparatus 10 through the network. The DICOM file 40 is transmitted to a primary storage memory 15 and is then stored in the primary storage memory 15. The control device 11 divides the DICOM file 40 into tag information 50 and image data 60. Since data indicating the amount of data in the tag information 50 is recorded in the tag information recording region 41, the tag information 50 includes the data indicating the amount of data. The image data 60 is recorded after the tag information 50. In this way, it is possible to divide the DICOM file 40 into the tag information 50 and the image data 60.

The divided tag information 50 is input to a first distributed data generation device 16. The first distributed data generation device 16 distributes the tag information 50 into a plurality of (n) first distributed tag information items, using the (k, n)-threshold secret sharing scheme. In this embodiment, the first distributed data generation device 16 {a (k, n)-threshold secret sharing device} distributes the tag information 50 into three distributed tag information items 51, 52, and 53 (the number of distributed tag information items may not be three). The distributed tag information items 51, 52, and 53 are transmitted to a distributed/recovered data storage memory 18 and is then temporarily stored in the distributed/recovered data storage memory 18.

The divided image data 60 is input to a second distributed data generation device 17. The second distributed data generation device 17 distributes the image data 60 into a plurality of (n) second image data items, using the (k, L, n)-threshold ramp secret sharing scheme. In this embodiment, the second distributed data generation device 17 {a (k, L, n)-threshold ramp sharing device} distributes the image data 60 into three image data items 61, 62, and 63 (the number of image data items may not be three). The distributed image data items 61, 62, and 63 are transmitted to the distributed/recovered data storage memory 18 and are then temporarily stored in the distributed/recovered data storage memory 18.

The distributed tag information items 51, 52, and 53 and the distributed image data items 61, 62, and 63 stored in the distributed/recovered data storage memory 18 are transmitted to a combination device 19 (a combination device). The combination device 19 combines the distributed tag information item 51 with the distributed image data item 61, combines the distributed tag information item 52 with the distributed image data item 62, and combines the distributed tag information item 53 with the distributed image data item 63 to generate combined data items 71, 72, and 73.

Among the generated combined data items 71, and 73, the combined data item 71 is transmitted to the first storage server 31 by a data communication device 22 (a distributed tag information transmission device and a distributed image data transmission device), the combined data item 72 is transmitted to the second storage server 32 by the data communication device 22, and the combined data item 73 is transmitted to the third storage server 33 by the data communication device 22. As such, the combined data items 71, 72, and 73 are transmitted to a plurality of different storage servers 31, 32, and 33 and are stored in the storage servers 31, 32, and 33.

FIG. 4 illustrates an example of a recording destination table indicating the recording destinations of the combined data items 71 to 73.

In the recording destination table, the addresses of the recording destinations of the combined data items 71 to 73 are stored for each DICOM file number (No.) and each DICOM file name.

The address (of a recording region) of the storage server 31 which is the recording destination of the combined data item 71, the address (of a recording region) of the storage server 32 which is the recording destination of the combined data item 72, and the address (of a recording region) of the storage server 33 which is the recording destination of the combined data item 73 are stored as a first recording destination, a second recording destination, and a third recording destination in the recording destination table so as to correspond to the file name of the DICOM file 40, respectively.

The recording destination table is stored in the memory 13. The recording destination table stored in the memory 13 is read to recognize the addresses of the recording destinations of the desired combined data items 71, 72, and 73, which makes it possible to read desired combined data from the storage servers 31, 32, and 33.

Figure 5:
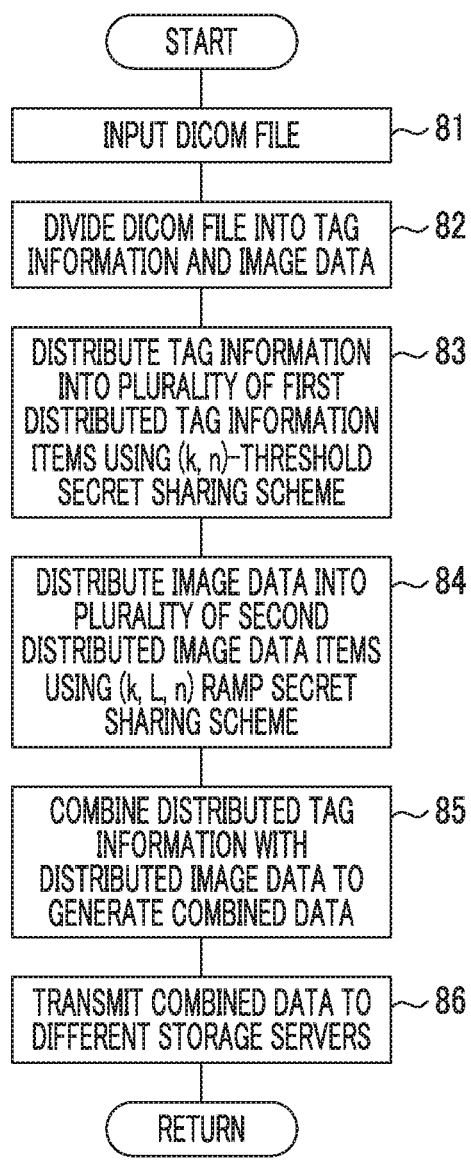
FIG. 5 is a flowchart illustrating the procedure of the image file distribution/recovery apparatus.

FIG. 5 is a flowchart illustrating the procedure of the image file distribution/recovery apparatus 10.

The DICOM file 40 transmitted from any one of the personal computers l to p is input from the data input/output device 14 (Step 81) and the control device 11 divides the DICOM file 40 into the tag information 50 and the image data 60 (Step 82). The first distributed data generation device 16 distributes the tag information 50 into the distributed tag information items 51, 52, and 53 (Step 83). The second distributed data generation device 17 distributes the image data 60 into the distributed image data items 61, 62, and 63 (Step 84).

As described above, the combination device 19 combines the distributed tag information item 51 with the distributed image data item 61, combines the distributed tag information item 52 with the distributed image data item 62, and combines the distributed tag information item 53 with the distributed image data item 63 to generate the combined data items 71, 72, and 73 (Step 85). The combined data item 71 is transmitted to the first storage server 31, the combined data item 72 is transmitted to the second storage server 32, and the combined data item 73 is transmitted to the third storage server 33 (Step 86).

In the above-described embodiment, for example, the combined data items 71 obtained by combining the distributed tag information items 51 and the distributed image data items 61 are transmitted to different storage servers 31. However, for example, the distributed tag information items 51 and the distributed image data items 61 may be transmitted to different storage servers 31, without being combined with each other. For example, the data communication device 22 (a distributed image data transmission device) transmits the distributed tag information item 51 that is not combined to the storage server 31, transmits the distributed tag information item 52 that is not combined to the storage server 32, and transmits the distributed tag information items 53 that is not combined to the storage server 33. The distributed image data item 61 may be transmitted to the storage server 31 or may be transmitted to a storage server other than the storage servers 31 to 33 in which the distributed tag information items 51 to 53 are stored. Similarly, the distributed image data item 62 may be transmitted to the storage server 32 or may be transmitted to a storage server other than the storage servers 31 to 33 in which the distributed tag information items 51 to 53 are stored. The distributed image data item 63 may be transmitted to the storage server 33 or may be transmitted to a storage server other than the storage servers 31 to 33 in which the distributed tag information items 51 to 53 are stored.

Figure 6:
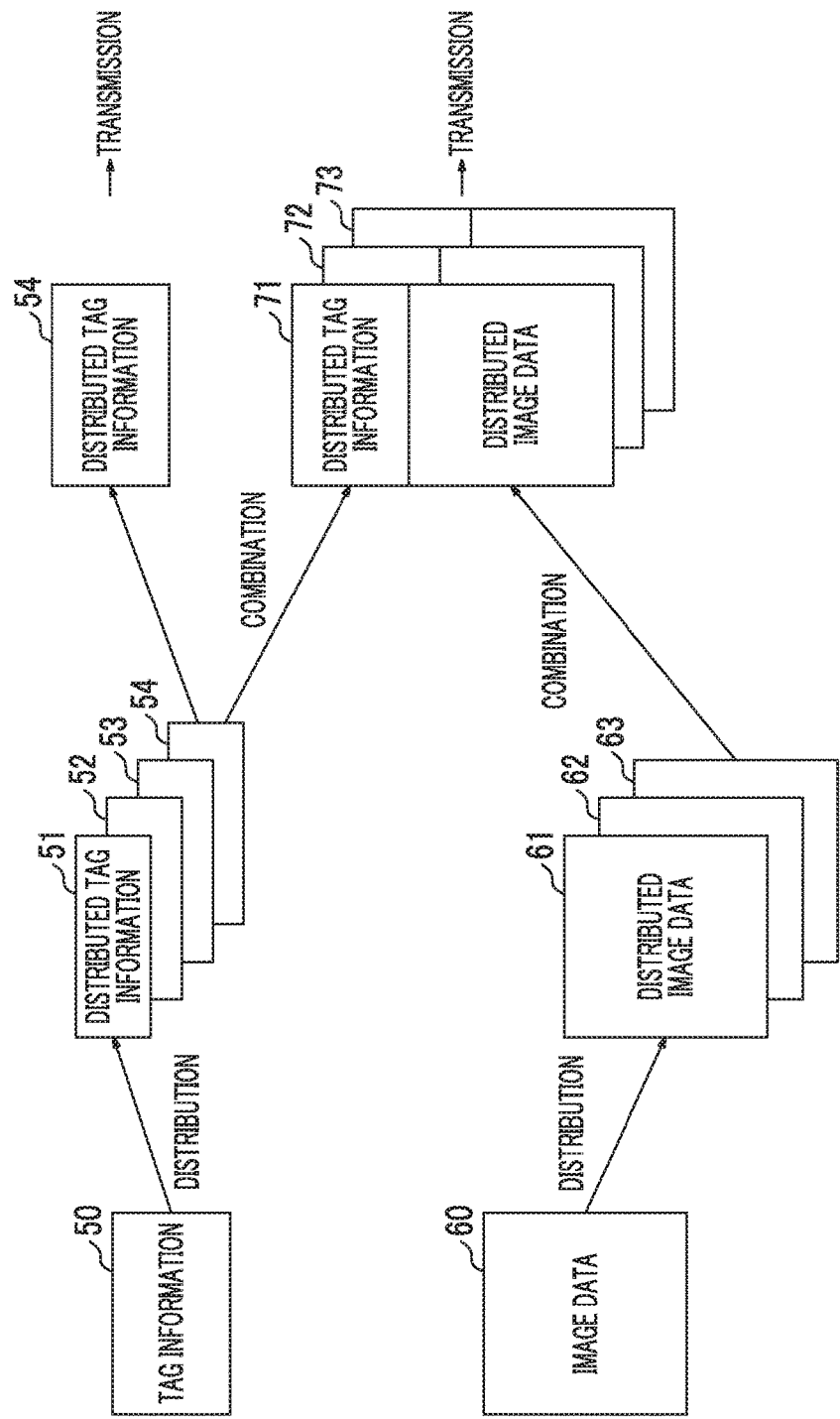
FIG. 6 is a flowchart illustrating the procedure of the image file distribution/recovery apparatus.

FIG. 6 corresponds to FIG. 3 and illustrates an aspect in which the image file distribution/recovery apparatus 10 distributes the DICOM file 40.

In the above-described embodiment, the number of distributed tag information items 51 to 53 (three distributed tag information items which are a plurality of first distributed tag information items) generated by the first distributed data generation device 16 is equal to the number of distributed image data items 61 to 63 (three distributed image data items which are a plurality of second distributed image data items) generated by the second distributed data generation device 17. However, the numbers may be different from each other.

Referring to FIG. 6, the first distributed data generation device 16 distributes the tag information 50 into four distributed tag information items 51 to 54. The second distributed data generation device 17 distributes the image data 60 into three distributed image data items 61 to 63. As described above, three distributed tag information items 51 to 53 among the distributed tag information items 51 to 54 distributed by the first distributed data generation device 16 are combined with the distributed image data items 61 to 63 distributed by the second distributed data generation device 17 to generate combined data items 71 to 73, respectively. As described above, the generated combined data items 71, 72, and 73 are transmitted to the storage servers 31, 32, and 33, respectively. Among the four distributed tag information items 51 to 54, the distributed tag information 54 that is not used to generate the combined data items 71 to 73 is transmitted to a storage server other than the storage servers 31 to 33 by the data communication device 22.

In the above-described embodiment, the number of distributed tag information items 51 to 54 generated by the first distributed data generation device 16 is greater than the number of distributed image data items 61 to 63 generated by the second distributed data generation device 17. However, the number of distributed tag information items may be less than the number of distributed image data items. In this case, the distributed image data item that is not used to generate the combined data items 71 to 73 is transmitted to a storage server other than the storage servers 31 to 33 to which the combined data items 71 to 73 have been transmitted.

Figure 7:
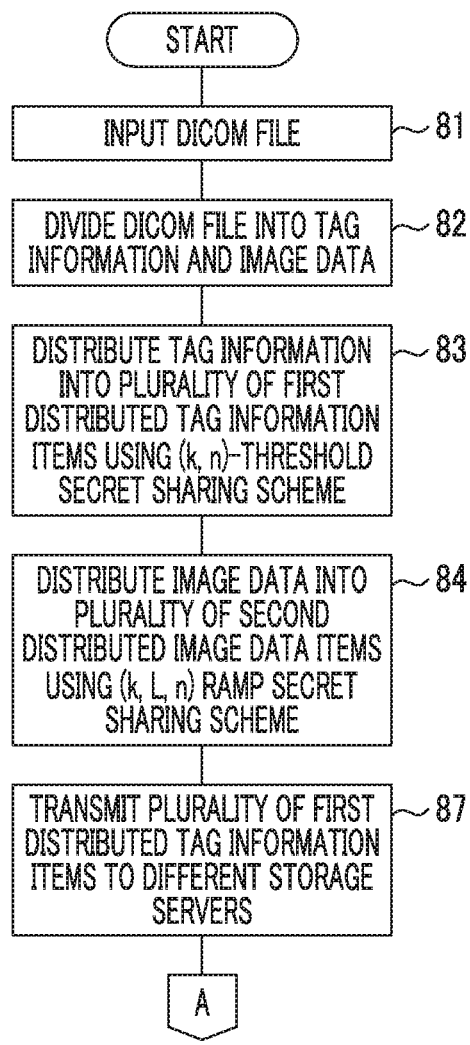
FIG. 7 is a flowchart illustrating the procedure of the image file distribution/recovery apparatus.
Figure 8:
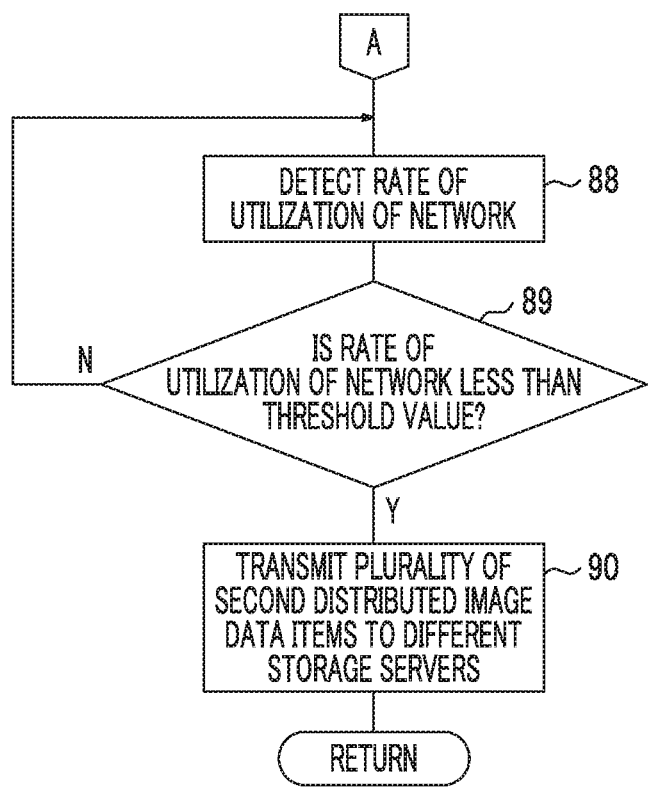
FIG. 8 is a flowchart illustrating the procedure of the image file distribution/recovery apparatus.

FIGS. 7 and 8 are flowcharts illustrating another procedure of the image file distribution/recovery apparatus 10. In the processes illustrated in FIGS. 7 and 8, the same processes as those illustrated in FIG. 5 are denoted by the same reference numerals and the description thereof will not be repeated.

As described above, three (a plurality of first) distributed tag information items 51 to 53 and three (a plurality of second) distributed image data items 61 to 63 are generated (Steps 81 to 84). The combined data items 71 to 73 are not generated and the data communication device 22 (a distributed tag information transmission device) transmits the three distributed tag information items 51, 52, and 53 to the storage servers 31, 32, and 33, respectively (Step 87).

When the distributed tag information items 51, 52, and 53 are transmitted to the storage servers 31, 32, and 33, respectively, the control device 11 detects the rate of utilization of the network connecting the image file distribution/recovers apparatus 10 and the storage servers 31 to 3n {the network (communication line) used to transmit a plurality of second distributed image data items by the data communication device 22} (Step 80). When the control device 11 (a determination device) determines that the detected rate of utilization is less than a threshold value (YES in Step 89), it is possible to rapidly transmit the distributed image data items 61 to 63 to the storage servers 31 to 3n, respectively. The data communication device 22 (a distributed image data transmission device) transmits a plurality of second distributed image data items 61, 62, and 63 to different storage servers among the storage servers 31 to 3n (Step 90). When the rate of utilization is equal to or greater than the threshold value (NO in Step 89), the transmission of the plurality of second distributed image data items 61, 62, and 63 is temporarily stopped until the rate of utilization is less than the threshold value. When the rate of utilization is less than the threshold value, the plurality of second distributed image data items 61. 62, and 63 are transmitted.

In the above-described embodiment, the rate of utilization of the network is detected and the distributed image data items 61 to 63 are transmitted to the storage servers 31 to 3n in a case in which the detected rate of utilization is less than the threshold value. However, even when the rate of utilization is not detected, the distributed tag information items 51 to 53 may be transmitted to different storage servers among the storage servers 31 to 3n and then the distributed image data items 61 to 63 may be transmitted to different storage servers among the storage servers 31 to 3n.

Figure 9:
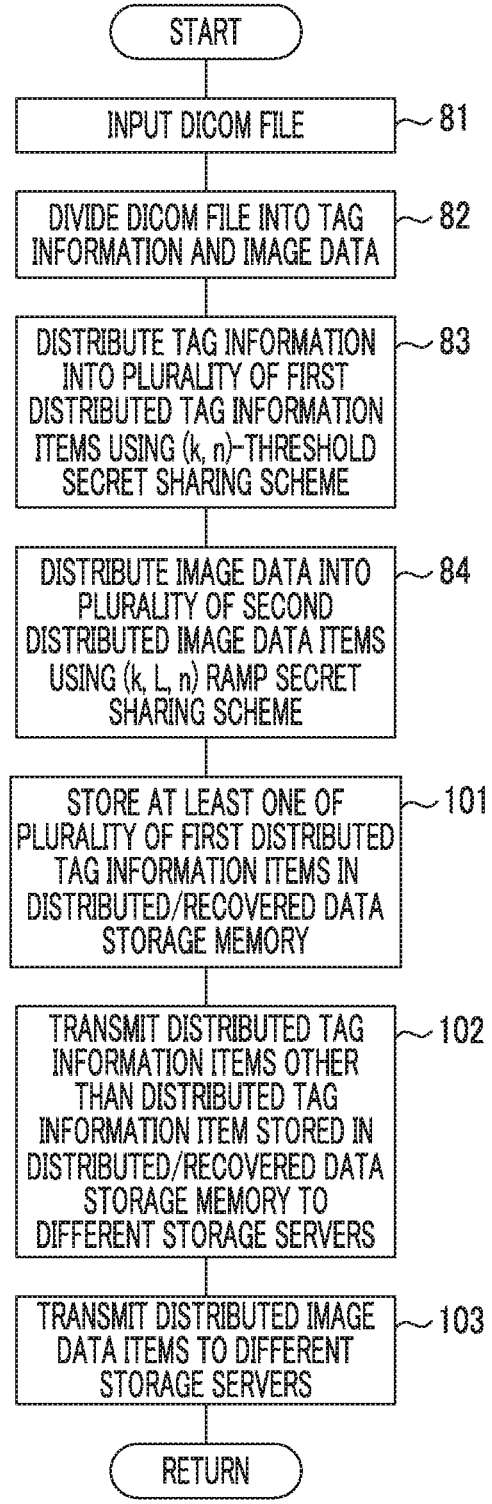
FIG. 9 is a flowchart illustrating the procedure of the image file distribution/recovery apparatus.

FIG. 9 is a flowchart illustrating still another procedure of the image file distribution/recovery apparatus 10. In FIG. 9, the same processes as those illustrated in FIG. 5 are denoted by the same reference numerals and the description thereof will not be repeated.

As illustrated in FIG. 6, the distributed tag information items 51 to 54 are generated and the distributed image data items 61 to 63 are generated (Steps 81 to 84). The distributed tag information 54 is stored in the distributed/recovered data storage memory 18, without being transmitted from the image file distribution/recovery apparatus 10 to any of the storage servers 31 to 3n (Step 101). As such, at least one of a plurality of first distributed tag information items is stored in the distributed/recovered data storage memory 18.

The data communication device 22 transmits the distributed tag information items 51 to 53 other than the distributed tag information 54 stored in the distributed/recovered data storage memory 18 to different storage servers among the storage servers 31 to 3n (Step 102). The data communication device 22 transmits the distributed image data items 61 to 63 to different storage servers among the storage servers 31 to 3n (Step 103).

Figure 10:
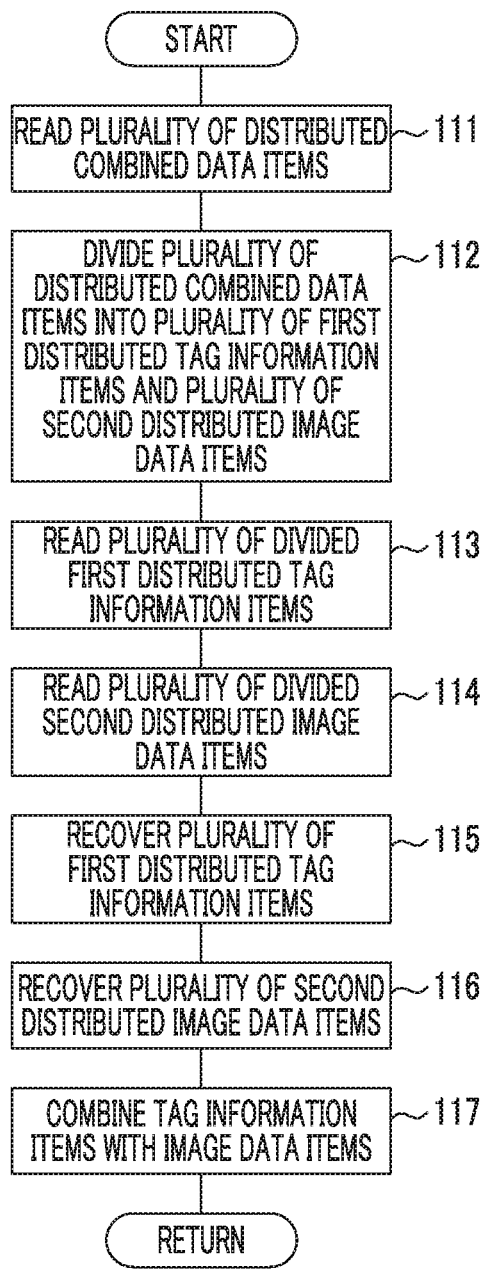
FIG. 10 is a flowchart illustrating the procedure of the image file distribution/recovery apparatus.
Figure 11:
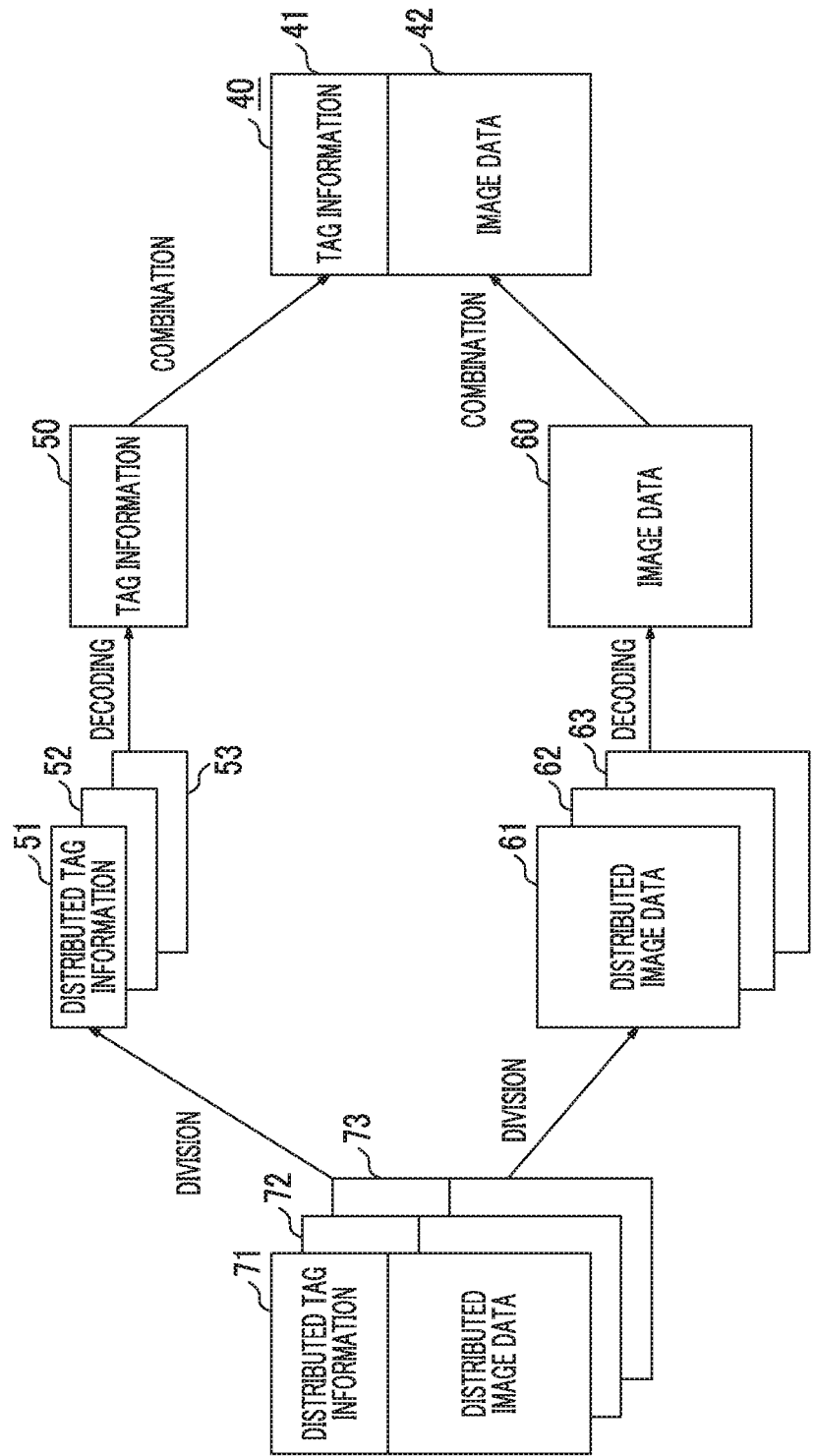
FIG. 11 illustrates an aspect in which the distributed combined data is recovered to the image file.
Figure 12:
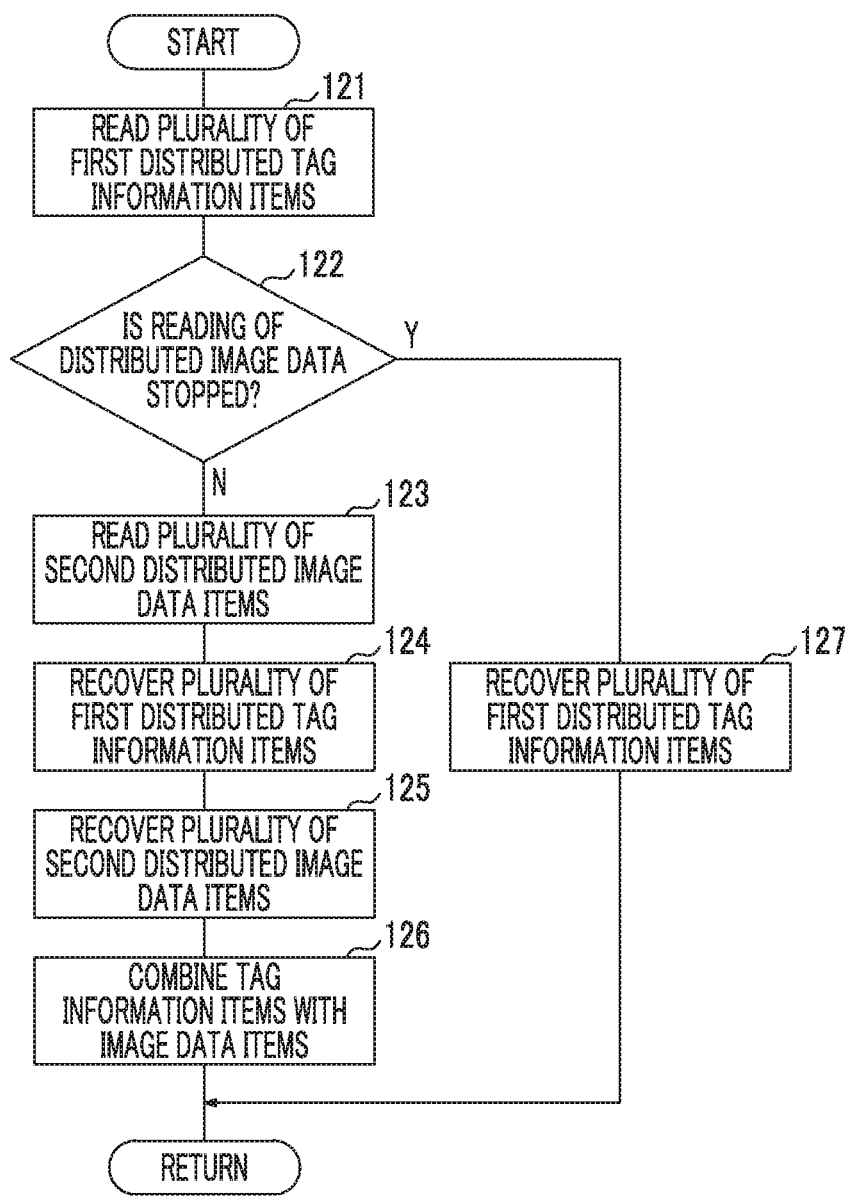
FIG. 12 is a flowchart illustrating the procedure of the image file distribution/recovery apparatus.

FIGS. 10 to 12 are diagrams illustrating an example in which the distributed tag information items 51 to 53 and the distributed image data items 61 to 63 that are distributed as described above are recovered.

FIG. 10 is a flowchart illustrating the procedure of the image file distribution/recovery apparatus 10. FIG. 11 illustrates an aspect in which the combined data items 71 and 73 (the distributed tag information items 51 to 53 and the distributed image data items 61 to 63) that are distributed as described above are recovered.

The distributed combined data items 71 to 73 are stored in different storage servers 31 to 33, respectively, such that the combined data item 71 is stored in the storage server 31, the combined data item 72 is stored in the storage server 32, and the combined data item 73 is stored in the storage server 33. As illustrated in FIG. 4, addresses indicating the storage destinations of the combined data items 71, 72, and 73 are stored in the memory 13. Therefore, the addresses are read and commands to transmit the combined data items 71, 72, and 73 are transmitted from the control device 11 of the image file distribution/recovery apparatus 10 to the storage servers 31, 32, and 33, respectively.

When the storage servers 31, 32, and 33 receive the transmission commands from the image file distribution/recovery apparatus 10, the storage server 31 transmits the combined data item 71 to the image file distribution/recovery apparatus 10, the storage server 32 transmits the combined data item 72 to the image file distribution/recovery apparatus 10, and the storage server 33 transmits the combined data item 73 to the image file distribution/recovery apparatus 10.

The data communication device 22 of the image file distribution/recovery apparatus 10 receives the combined data items 71 to 73 transmitted from the storage servers 31 to 33. That is, the data communication device 22 reads a plurality of combined data items 71 to 73 (Step 111).

The control device 11 divides the combined data items 71 to 73 into a plurality of first distributed tag information items 51 to 53 and a plurality of second distributed image data items 61 to 63, respectively (Step 112). The division positions of each of the distributed tag information items 51 to 53 and each of the distributed image data items 61 to 63 are known by storing the amount of data in each of the distributed tag information items 51 to 53 in the memory 13 at the time of distribution and by storing the start positions of the distributed image data items 61 to 63 in the memory 13. Each of the divided distributed tag information items 51 to 53 and each of the divided distributed image data items 61 to 63 are temporarily stored in the distributed/recovered data storage memory 18.

The control device 11 reads the distributed tag information items 51 to 53 temporarily stored in the distributed/recovered data storage memory 18 and transmits the distributed tag information items 51 to 53 to a first distributed data recovery device 20. That is, the control device 11 (a distributed tag information reading device) reads a plurality of divided first distributed tag information items 51 to 53 (Step 113). As such, the tag information recorded in the tag information recording region 41 of the DICOM file 40 is distributed into a plurality of first distributed tag information items 51 to 53 by the (k, n)-threshold secret sharing scheme, the plurality of first distributed tag information items 51 to 53 are stored in different storage servers 31 to 33, and the control device 11 (a distributed tag information reading device) reads the plurality of first distributed tag information items 51 to 53.

The control device 11 reads the distributed image data items 61 to 63 temporarily stored in the distributed/recovered data storage memory 18 and transmits the distributed image data items 61 to 63 to a second distributed data recovery device 21. That is, the control device 11 (a distributed image data reading device) reads a plurality of divided second distributed image data items 61 to 63 (Step 114). As such, the image data recorded in the image data recording region 42 of the DICOM file 40 is distributed into a plurality of second distributed image data items 61 to 63 by the (k, L, n)-threshold ramp secret sharing scheme, the plurality of second distributed image data items 61 to 63 are stored in different storage servers 31 to 33, and the control device 11 (a distributed image data reading device) reads the plurality of second distributed image data items 61 to 63.

The first distributed data recovery device 20 recovers the distributed tag information items 51 to 53 (a plurality of first distributed tag information items) (Step 115). The first distributed data recovery device 20 (a distributed tag information recovery device) recovers the first distributed tag information read by the control device 11 (a distributed tag information reading device) using the (k, n)-threshold secret sharing scheme. The tag information 50 before distribution is obtained by the recovery.

The second distributed data recovery device 21 recovers the distributed image data items 61 to 63 (a plurality of second distributed image data items) (Step 116). The second distributed data recovery device 21 (a distributed image data recovery device) recovers the plurality of second distributed image data items 61 to 63 read by the control device 11 (a distributed image data reading device) using the (k, L, n)-threshold ramp secret sharing scheme. The image data 60 before distribution is obtained by the recovery.

The control device 11 reads the recovered tag information 50 and the recovered image data 60. The control device 11 (an image file generation device) combines the tag information 50 and the image data 60 to generate the DICOM file 40 (Step 117). The generated DICOM file 40 is transmitted to any one of the personal computers 1 to n and the image and the tag information are reproduced.

In the above-described embodiment, the combined data items 71 to 73 stored in different storage servers 31 to 33 are read and recovered to the DICOM file 40. In a case in which the distributed tag information items 51 to 53 and the distributed image data items 61 to 63 which are not combined with each other are stored in different storage servers 31 to 33, the distributed tag information items 51 to 53 can be read by the data communication device 22 (a distributed tag information reading device) and the distributed image data items 61 to 63 can be read by the communication device 22 (a distributed image data reading device). Similarly, the distributed tag information items 51 to 53 and the distributed image data items 61 to 63 can be recovered to the image tile. In addition, in a case in which the distributed tag information items 51 to 53 are stored in different storage servers 31 to 33 and the distributed image data items 61 to 63 are distributed and stored in a storage server other than the storage servers 31 to 33, similarly, the distributed tag information items 51 to 53 and the distributed image data items 61 to 63 can be recovered to the DICOM file 40.

FIG. 12 illustrates yet another procedure and is a flowchart illustrating the procedure of the image file distribution/recovery apparatus 10.

In the procedure illustrated in FIG. 12, after the distributed tag information items 51 to 53 are read, the distributed image data items 61 to 63 are read.

Similarly to the above, the data communication device 22 reads a plurality of first distributed tag information items 51 to 53 stored in the storage servers 31 to 33 (Step 121).

The user may recover only the distributed tag information items 51 to 53. In a case in which it is considered that the distributed image data items 61 to 63 do not need to be recovered, the user inputs a read stop command to the image file distribution/recovery apparatus 10 through the operation device 12. When the read stop command is input (YES in Step 122), the control device 11 (an image data reading stop device) controls the data communication device 22 such that the reading of the distributed image data items 61 to 63 is stopped. The first distributed data recovery device 20 recovers the read distributed tag information items 51 to 53 (Step 127).

In a case in which it is considered that the distributed image data items 61 to 63 need to be recovered, the read stop command is not input to the image file distribution/recovery apparatus 10 (NO in Step 122). Similarly to the above, the data communication device 22 reads the distributed image data items 61 to 63 stored in the storage servers 31 to 33 (Step 123). The first distributed data recovery device 20 recovers the read distributed tag information items 51 to 53 to obtain the tag information 50 (Step 124). The second distributed data recovery device 21 recovers the read distributed image data items 61 to 63 to obtain the image data 60 (Step 125). The tag information 50 and the image data 60 are combined to obtain the DICOM file 40 (Step 126).

As described above, in a case in which the tag information 50 is divided into a plurality of distributed tag information items 51 to 54, the distributed tag information item 54 is stored in the distributed/recovered data storage memory 18, and the distributed tag information items 51 to 53 are stored in the storage servers 31 to 33, the tag information 50 and the image data 60 may be recovered by the same method as described above.

In the image file distribution/recovery apparatus 10 illustrated in FIG. 1, an image file is distributed and recovered by hardware. Some or all of the distribution and recovery processes may be performed by software. In addition, the image file distribution/recovery apparatus 10 can perform both the distribution and recovery of an image file. However, an apparatus that performs only the distribution of an image file and an apparatus that performs only the recovery of an image file may be separately provided.

In the above-described embodiment, the tag information recorded in the tag information recording region of the image file is distributed by the (k, n)-threshold secret sharing scheme. However, the name of the region in which the tag information is recorded is not limited to the tag information recording region and management information of the image file, such as header information recorded in a header recording region, may be distributed by the (k, n)-threshold secret sharing scheme.

What is claimed is:

1. An image file distribution method, said method comprising the steps of:
   allowing a (k, n)-threshold secret sharing device to distribute tag information recorded in a tag information recording region of an image file into a plurality of first distributed tag information items, using a (k, n)-threshold secret sharing scheme;
   allowing a (k, L, n)-threshold ramp secret sharing device to distribute image data recorded in an image data recording region of the image file into a plurality of second distributed image data items, using a (k, L, n)-threshold ramp secret sharing scheme;
   allowing a distributed tag information transmission device to transmit each of the plurality of first distributed tag information items distributed by the (k, n)-threshold secret sharing device to different storage servers; and
   allowing a distributed image data transmission device to transmit each of the plurality of second distributed image data items distributed by the (k, L, n)-threshold ramp secret sharing device to different storage servers.

2. An image tile recovery method, said method comprising the steps of:
   allowing a distributed tag information reading device to read a plurality of first distributed tag information items which have been obtained by distributing tag information recorded in a tag information recording region of an image file, using a (k, n)-threshold secret sharing scheme, and have been stored in different storage servers;
   allowing a distributed image data reading device to read a plurality of second distributed image data items which have been obtained by distributing image data recorded in an image data recording region of the image tile, using a (k, L, n)-threshold ramp secret sharing scheme, and have been stored in different storage servers;
   allowing a distributed tag information recovery device to recover the plurality of first distributed tag information items read by the distributed tag information reading device, using the (k, n)-threshold secret sharing scheme; and
   allowing a distributed image data recovery device to recover the plurality of second distributed image data items read by the distributed image data reading device, using the (k, L, n)-threshold ramp secret sharing scheme.

3. A non-transitory recording medium storing a computer-readable program that controls a computer of an image file distribution apparatus such that the computer performs:
   distributing tag information recorded in a tag information recording region of an image file into a plurality of first distributed tag information items, using a (k, n)-threshold secret sharing scheme;
   distributing image data recorded in an image data recording region of the image file into a plurality of second distributed image data items, using a (k, L, n)-threshold ramp secret sharing scheme;
   transmitting each of the plurality of first distributed tag information items to different storage servers; and
   transmitting each of the plurality of second distributed image data items distributed by the (k, L, n)-threshold ramp secret sharing scheme to different storage servers.

4. A non-transitory recording medium storing a computer-readable program that controls a computer of an image file recovery apparatus such that the computer performs:
   reading a plurality of first distributed tag information items which have been obtained by distributing tag information recorded in a tag information recording region of an image file, using a (k, n)-threshold secret sharing scheme, and have been stored in different storage servers;
   reading a plurality of second distributed image data items which have been obtained by distributing image data recorded in an image data recording region of the image file, using a (k, L, n)-threshold ramp secret sharing scheme, and have been stored in different storage servers;
   recovering the read plurality of first distributed tag information items, using the (k, n)-threshold secret sharing scheme; and
   recovering the read plurality of second distributed image data items, using the (k, L, n)-threshold ramp secret sharing scheme.

5. An image file distribution apparatus comprising:
   a processor configured for:
   allowing a (k, n)-threshold secret sharing device to distribute tag information recorded in a tag information recording region of an image file into a plurality of first distributed tag information items, using a (k, n)-threshold secret sharing scheme;
   allowing a (k, L, n)-threshold ramp secret sharing device to distribute image data recorded in an image data recording region of the image file into a plurality of second distributed image data items, using a (k, L, n)-threshold ramp secret sharing scheme;
   allowing a distributed tag information transmission device to transmit each of the plurality of first distributed tag information items distributed by the (k, n)-threshold secret sharing device to different storage servers; and
   allowing a distributed image data transmission device to transmit each of the plurality of second distributed image data items distributed by the (k, L, n)-threshold ramp secret sharing device to different storage servers.

6. An image file recovery apparatus comprising:
   a processor configured for:
   allowing a distributed tag information reading device to read a plurality of first distributed tag information items which have been obtained by distributing tag information recorded in a tag information recording region of an image file, using a (k, n)-threshold secret sharing scheme, and have been stored in different storage servers;

allowing a distributed image data reading device to read a plurality of second distributed image data items which have been obtained by distributing image data recorded in an image data recording region of the image file, using a (k, L, n)-threshold ramp secret sharing scheme, and have been stored in different storage servers;

allowing a distributed tag information recovery device to recover the plurality of first distributed tag information items read by the distributed tag information reading device, using the (k, n)-threshold secret sharing scheme; and allowing a distributed image data recovery device to recover the plurality of second distributed image data items read by the distributed image data reading device, using the (k, L, n)-threshold ramp secret sharing scheme.

\* \* \* \* \*